(12) United States Patent
Hossain et al.

(10) Patent No.: US 11,439,533 B2
(45) Date of Patent: Sep. 13, 2022

(54) EYE DROP DISPENSING APPARATUS

(71) Applicants: Syed Shadman Hossain, Herndon, VA (US); Syed Shayan Hossain, Herndon, VA (US)

(72) Inventors: Syed Shadman Hossain, Herndon, VA (US); Syed Shayan Hossain, Herndon, VA (US)

( * ) Notice: Subject to any disclaimer, the term of this patent is extended or adjusted under 35 U.S.C. 154(b) by 61 days.

(21) Appl. No.: 16/508,976

(22) Filed: Jul. 11, 2019

(65) Prior Publication Data
US 2020/0276048 A1 Sep. 3, 2020

Related U.S. Application Data

(60) Provisional application No. 62/811,933, filed on Feb. 28, 2019.

(51) Int. Cl.
*A61F 9/00* (2006.01)
(52) U.S. Cl.
CPC .......... *A61F 9/0008* (2013.01); *A61F 9/0026* (2013.01)
(58) Field of Classification Search
CPC .............................. A61F 9/0008; A61F 9/0026
See application file for complete search history.

(56) References Cited

U.S. PATENT DOCUMENTS

| 4,733,802 | A | * | 3/1988 | Sheldon | A61F 9/0026 222/185.1 |
| 7,563,256 | B2 | * | 7/2009 | Hearne | A61F 9/0008 604/300 |
| 2020/0324945 | A1 | * | 10/2020 | Song | B65D 35/22 |

* cited by examiner

*Primary Examiner* — Benjamin J Klein
(74) *Attorney, Agent, or Firm* — Hunton Andrews Kurth LLP

(57) ABSTRACT

An ophthalmic solution discharging apparatus is described. The ophthalmic solution discharging apparatus comprises: a base portion comprising a cylindrical base for receiving and removably engaging a dropper of an ophthalmic solution container; a head portion comprising a micro nozzle portion through which ophthalmic solution is discharged, a shield portion that cylindrically surrounds the micro nozzle portion, the shield portion comprising a wall containing an opening for viewing a portion of the micro nozzle portion during discharge; a neck portion that connects the base portion and the head portion; and an internal cavity portion defined by the base, head and neck portions and comprising a (1) container engagement portion for receiving and removably engaging the ophthalmic solution container, and (2) funnel portion for transporting and discharging ophthalmic solution through the micro nozzle portion at a lesser volume than would otherwise be discharged by the dropper of the ophthalmic solution container.

8 Claims, 4 Drawing Sheets

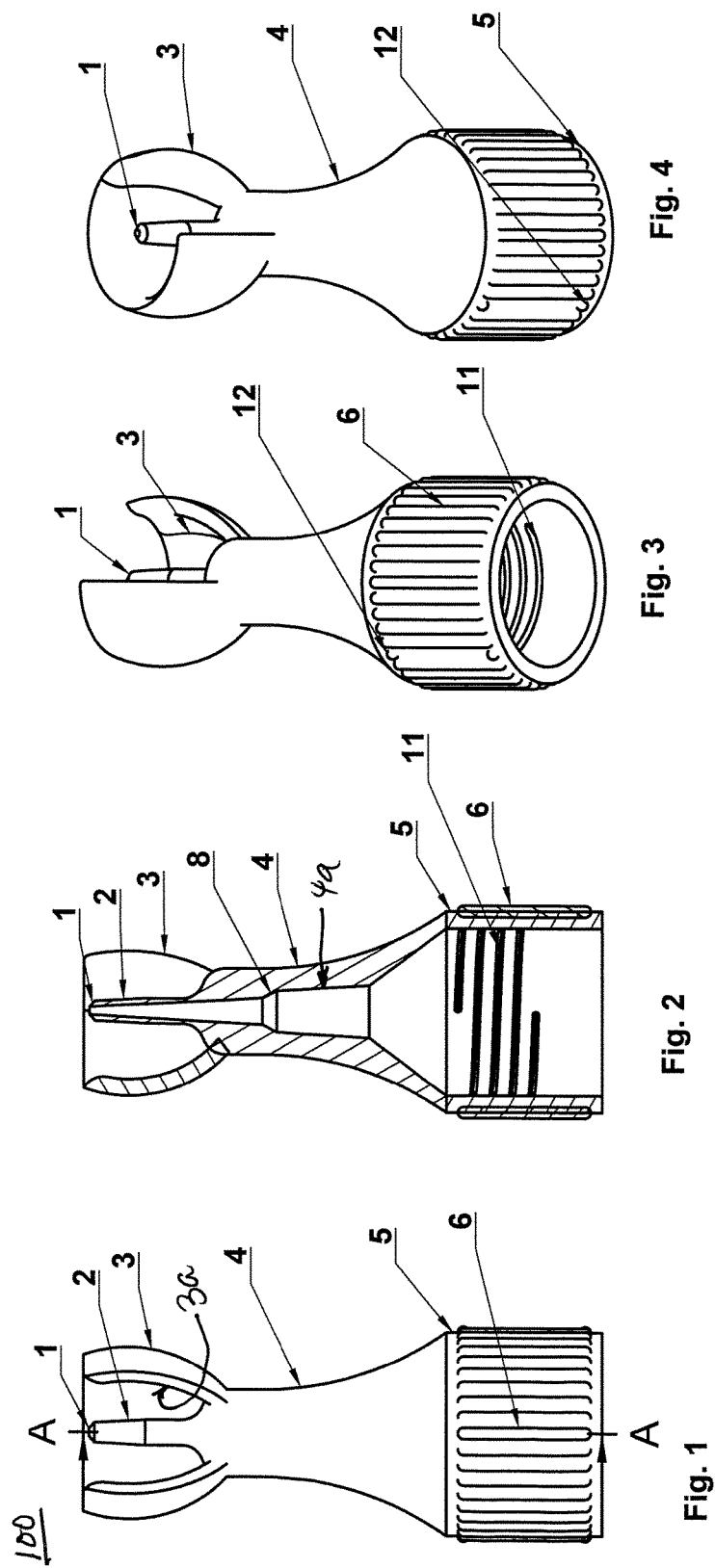

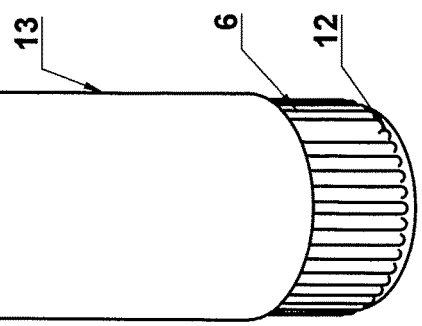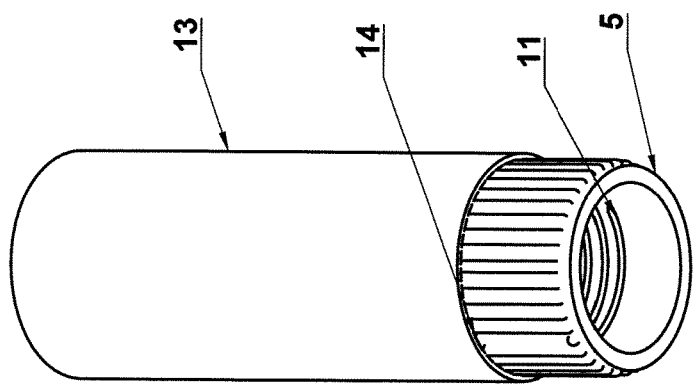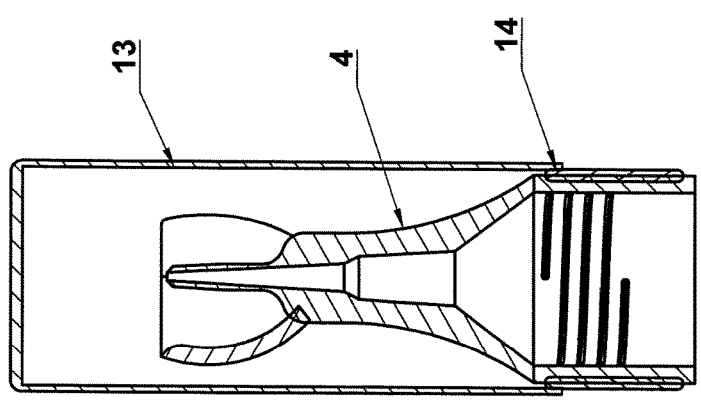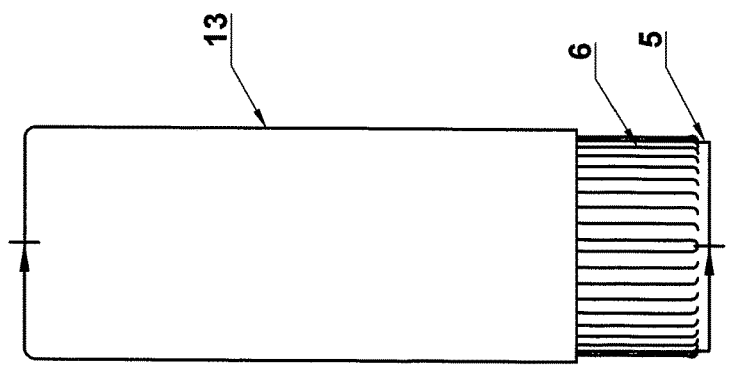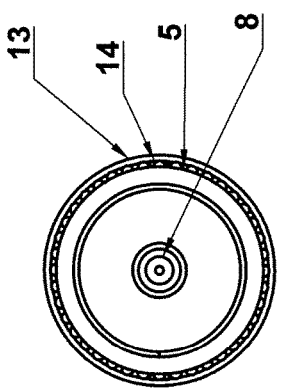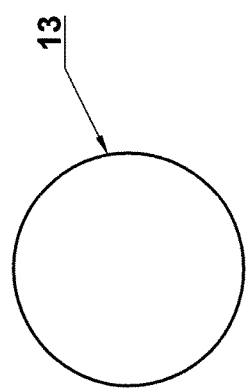

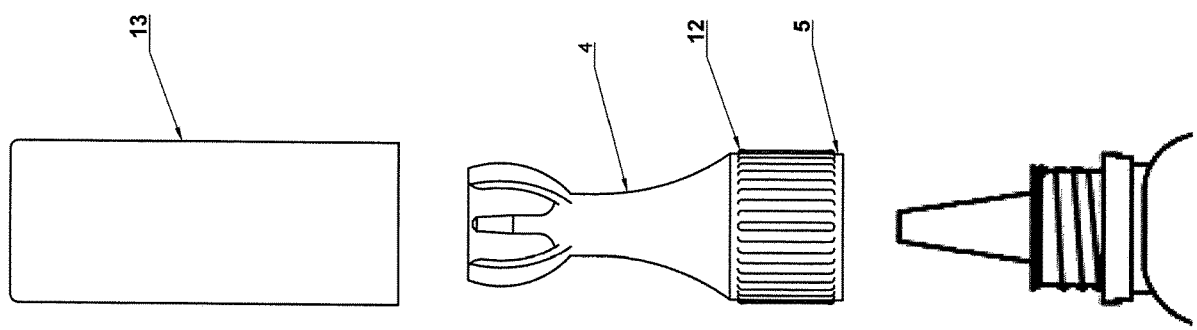

EYE DROP DISPENSING APPARATUS

CROSS REFERENCE TO RELATED APPLICATIONS

This application claims priority to U.S. Provisional Application No. 62/811,933, filed Feb. 28, 2019, the contents of which are incorporated herein in its entirety.

FIELD OF THE INVENTION

This invention relates generally to the field of ophthalmic drug delivery devices, and more particularly to an eye dropper apparatus that optimizes the delivery of ophthalmic drugs and solutions by reducing drop volume to an efficient amount more suitable for the human eye.

BACKGROUND OF THE INVENTION

Eye drop dispensers are well known devices for delivering ophthalmic drugs or solutions. Existing eye drop dispensers, however, are not designed to deliver an efficient amount of drug or solution, nor do they facilitate patient self-delivery and drop follow through. For example, according to the American Academy of Ophthalmology and the National Public Radio, existing eye drop dispensers discharge single drop volumes between 25-50 µL, much more than the 7-10 µL the human eye is capable of absorbing. Any discharged amount of drug or solution beyond 7-10 µL is effectively wasted. Moreover, existing eye drop dispensers can also cause injury when used improperly. The elderly, for example, can harm themselves by inadvertently having the sharp tip of the come into contact with the eye during application.

These and other problems exist.

SUMMARY OF THE INVENTION

An object of the present invention is to overcome the aforementioned and other drawbacks existing in the prior art.

A further objective of the invention is to provide an eye drop dispenser that discharges a volume of approximately 7-15 µL of ophthalmic drugs or solution and decreases waste of expensive medicine.

Another objective of the invention is to protect against injury to the user.

Yet another benefit of the invention is its adaptability to existing eye drop dispensers.

According to an embodiment of the claimed invention, an ophthalmic drug or solution discharging apparatus is provided. The apparatus comprises a base portion comprising a cylindrical base for receiving and removably engaging a dropper of an ophthalmic solution container. The apparatus also comprises a head portion comprising a micro nozzle portion through which ophthalmic solution is discharged, and a shield portion that cylindrically surrounds the tip portion, the shield portion comprising a wall containing an opening for viewing a portion of the micro nozzle portion during discharge. In addition, a neck portion connecting the base portion and the head portion, the neck portion possessing a wider diameter at the base portion and a narrower diameter at the head portion. The apparatus also provides an internal cavity portion defined by the base, head and neck portions, wherein the internal cavity portion comprises a (1) container engagement portion for receiving and removably engaging the ophthalmic solution container, and (2) a funnel portion for transporting and discharging ophthalmic solution at a lesser volume than would otherwise be discharged by the dropper of the ophthalmic solution container.

The accompanying drawings, which are incorporated in and constitute a part of this specification, illustrate various embodiments of the invention and, together with the description, serve to explain the principles of the invention.

BRIEF DESCRIPTION OF THE DRAWINGS

FIG. 1 is a front view of an eye drop dispenser, according to an embodiment of the invention;

FIG. 2 is a cross-section view of an eye drop dispenser, according to an embodiment of the invention;

FIG. 3 is an isometric view of an eye drop dispenser, according to an embodiment of the invention;

FIG. 4 is an isometric view of an eye drop dispenser, according to an embodiment of the invention;

FIG. 5 is a top view of an eye drop dispenser, according to an embodiment of the invention;

FIG. 6 is a bottom view of an eye drop dispenser, according to an embodiment of the invention;

FIG. 7 is a front view of an eye drop dispenser and cap, according to an embodiment of the invention;

FIG. 8 is a cross-section view of an eye drop dispenser and cap, according to an embodiment of the invention;

FIG. 9 is an isometric view of an eye drop dispenser and cap, according to an embodiment of the invention;

FIG. 10 is an isometric view of an eye drop dispenser and cap, according to an embodiment of the invention;

FIG. 11 is a top view of an eye drop dispenser and cap, according to an embodiment of the invention;

FIG. 12 is a bottom view of an eye drop dispenser and cap, according to an embodiment of the invention;

FIG. 13 is an assembly of an eye drop dispenser, ophthalmic solution container and cap, according to an embodiment of the invention.

DETAILED DESCRIPTION OF THE INVENTION

Figure 14:
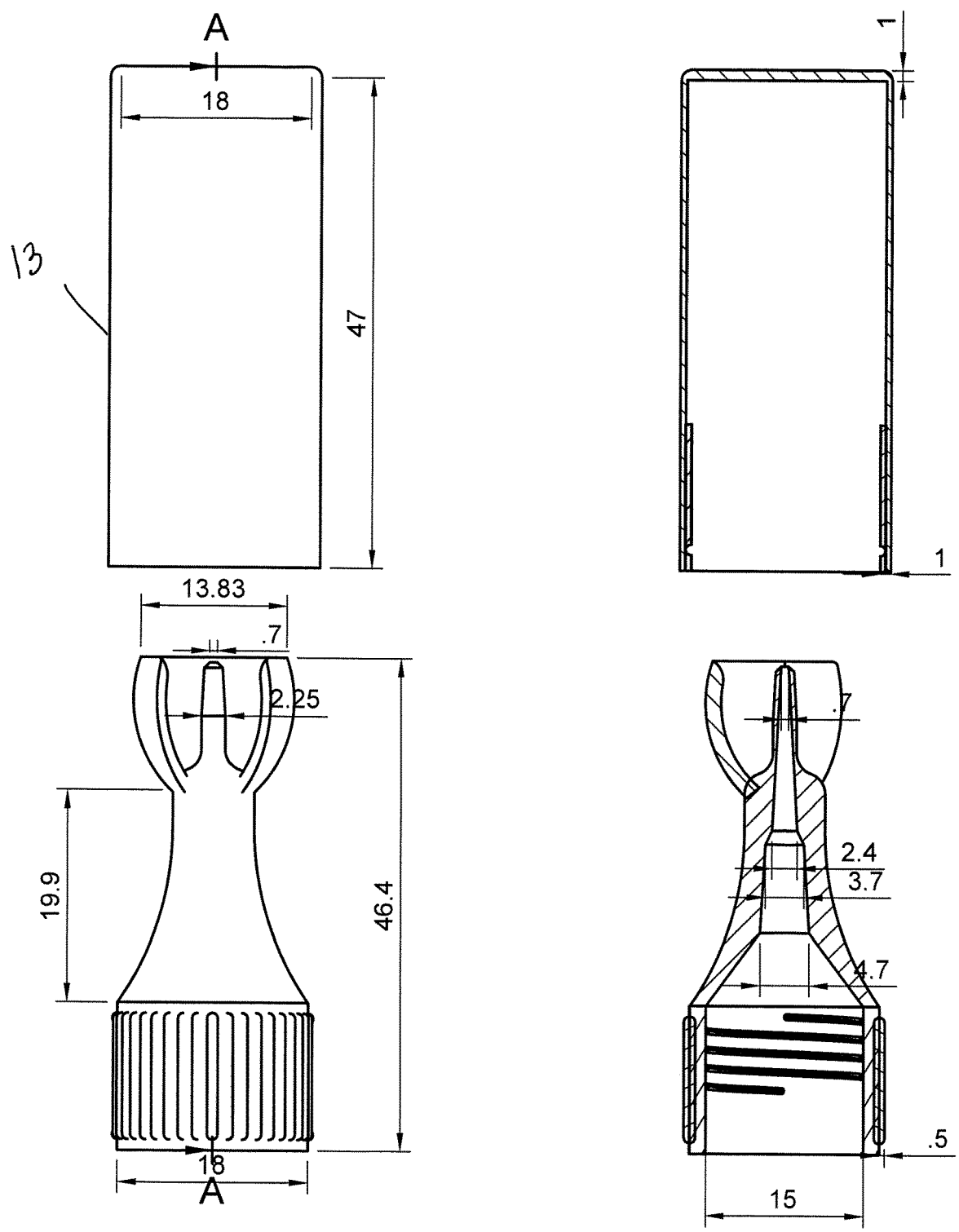
FIG. 14 is a depiction of the dimensions of an eye drop dispenser and cap, according to an embodiment of the invention.

Reference will now be made to the present preferred embodiments of the invention, examples of which are illustrated in the accompanying drawings in which like reference characters refer to corresponding elements.

As described herein, the invention may comprise an eye drop device designed to deliver a specific volume of ophthalmic solution (e.g., saline, drug, medication, or other liquid). In some embodiments, the invention may contain a threaded, base attachment portion, a neck portion, and a micro nozzle portion with a protective, curved wall. The device may, in some embodiments, be removably engaged (e.g., screwed, snapped or otherwise attached) onto an eye drop bottle. In other embodiments, the eye drop device be incorporated into the design of the bottle. The device may also comprise a removable attachment cap to protect the micro nozzle portion when not in use or in storage. The cap may primarily cover the micro nozzle and curvature areas. In some embodiments, the curvature portion near the micro nozzle may serve to protect the user's eye from risks of harm from the sharp micro nozzle. The curvature may also comprise a cut-out portion in so that the user is able to see liquid accumulate near the micro nozzle before delivery, as well as for the discharged drop to have an untouched passage into the eye. In some embodiments, the dimensions of the micro nozzle are designed to dispense a drop volume of approximately 7-10 μL.

FIG. 1 is a front view of an eye drop dispenser 100, according to an embodiment of the invention. As shown, the drop dispenser 100 consists of three main parts—a base 5, a neck 4 connecting the base with the opening micro nozzle 2 (which employs the main, discharging hole of the device 1), and an eye-shield 3. Eye shield 3 may also contain a cut-out 3a which enables a user to see liquid accumulate near the micro nozzle 2 before delivery, as well as for the discharged drop to have an untouched passage into the eye In some embodiments, the base may contain extruding ridges 6 for user comfort to screw on the device onto an eye drop bottle or container (as shown in FIG. 13). In some embodiments, eye drop dispenser 100 may be made of a soft, flexible, or durable material, such as, for example, silicone or thermoplastic polyurethane. Other materials are contemplated. Eye dispenser 100 may be manufactured through molding, extrusion, 3D printing, or other manufacturing process or technique.

FIG. 2 is a cross-section view of an eye drop dispenser 100, according to an embodiment of the invention. In the interior of the neck 4, an inner needle 4a may be formed. The inner needle 4a may comprise a cavity or channel, for example, that transports a liquid drop using a series of refining, miniature funnel shapes 8 that compress, channel or funnel the drop in order to discharge a reduced drop volume through nozzle 2 and hole 1. Preferably, the discharged volume is between 7-10 μl, but other volumes are possible and contemplated, such as, for example, 10-15 μl. As shown, inner needle 4a includes four miniature funnel shapes which collectively taper down to discharging hole 1. In some embodiments, the tapering of the respective miniature funnels may vary, as shown.

As shown in FIGS. 2 and 3, for example, the interior of base 5 may include threads 11 which allow for assembly or attachment of the eye dispenser 100 to a customary ophthalmic drug dispenser, such as shown in FIG. 13, for example. Additionally, as shown in FIG. 2, base 5 may include two extruding spheres 12 on either side of the device, totaling to 4 on the whole device, to allow for a clicking-on mechanism of the cap for this invention (see FIGS. 7-10). Once the cap 13 is attached onto the attachment device (as shown in FIGS. 8 and 12), a joint 14 is formed, which is the cap's concaved section near the bottom of the cap, permitting the sphere(s) 12 to fit in and seal the joint between the cap 13 and the device.

FIG. 3 is an isometric view of an eye drop dispenser 100, according to an embodiment of the invention. FIG. 4 is another isometric view of an eye drop dispenser 100, according to an embodiment of the invention. FIG. 5 is a top view of an eye drop dispenser 100, according to an embodiment of the invention. FIG. 6 is a bottom view of an eye drop dispenser 100, according to an embodiment of the invention. FIG. 7 is a front view of an eye drop dispenser 100 and cap 13, according to an embodiment of the invention. FIG. 8 is a cross-section view of an eye drop dispenser 100 with cap 13, according to an embodiment of the invention. FIG. 9 is an isometric view of an eye drop dispenser 100 and cap 13, according to an embodiment of the invention. FIG. 10 is an isometric view of an eye drop dispenser 100 and cap 13, according to an embodiment of the invention. FIG. 11 is a top view of the eye drop dispenser 100 and cap 13, according to an embodiment of the invention. FIG. 12 is a bottom view of an eye drop dispenser and cap, according to an embodiment of the invention. FIG. 13 depicts an alignment for assembly of an eye drop dispenser 100, ophthalmic solution container and cap 13, according to an embodiment of the invention.

FIG. 14 is a depiction of the exemplary dimensions of an eye drop dispenser and cap, according to an embodiment of the invention. For example, the length and width of the cap 13 is 47 mm and 18 mm, respectively. Eye dropper device 100 has length and width of 46.4 mm and 18 mm, respectively, while neck 4 is 19.99 mm in length, cut-out 3a is 2.25 mm wide, and width of the discharging hole 1 is 0.7 mm wide. The internal widths of the various miniature funnels 8, base 5 and the thickness of the device 100 and cap 13 are as shown. While the dimensions shown are in millimeters, other units of measurement are contemplated. Other dimensions for the eye dropper and cap are possible and contemplated.

Other embodiments, uses and advantages of the present invention will be apparent to those skilled in the art from consideration of the specification and practice of the invention disclosed herein. The specification and examples should be considered exemplary only. The intended scope of the invention is only limited by the claims appended hereto.

What is claimed is:

1. An ophthalmic drug or solution discharging apparatus, comprising:
   a base portion comprising a cylindrical base for receiving and removably engaging a dropper of an ophthalmic solution container;
   a head portion comprising a tip portion through which ophthalmic solution is discharged, and a shield portion that cylindrically surrounds the tip portion, the shield portion comprising a wall containing an opening for viewing a portion of the tip portion during discharge;
   a neck portion connecting the base portion and the head portion, the neck portion possessing a wider diameter at the base portion and a narrower diameter at the head portion; and
   an internal cavity portion defined by the base, head and neck portions, wherein the internal cavity portion comprises a (1) container engagement portion for receiving and removably engaging the dropper of an ophthalmic solution container, and (2) a funnel portion for receiving, transporting and discharging ophthalmic solution at a lesser volume than would otherwise be discharged by the dropper of the ophthalmic solution container, wherein a diameter of the funnel portion consistently narrows in the direction of ophthalmic solution discharge flow, and wherein a portion of the funnel portion for dispensing the ophthalmic solution is longer than a portion of the funnel portion for receiving the ophthalmic solution.

2. The ophthalmic drug or solution discharging apparatus of claim 1 wherein the tip portion comprises a tubular shape allowing for an approximate drop discharge between 10 μL-15 μL in volume.

3. The ophthalmic drug or solution discharging apparatus of claim 1 wherein said shield portion comprises a curved wall.

4. The ophthalmic drug or solution discharging apparatus of claim 1 further comprising a cap for removable attachment to the base portion.

5. The ophthalmic drug or solution discharging apparatus of claim 4 wherein the cap attaches onto extruding spheres on either side of the base portion.

6. The ophthalmic-drug-discharging attachment of claim 1, wherein the aforementioned neck and head are made of silicone or thermoplastic polyurethane material.

7. The ophthalmic drug or solution discharging apparatus of claim 6, wherein the silicone or thermoplastic polyurethane material being of at least one transparent or opaque color that allows users or patients to view their drug accumulating for discharging.

8. The ophthalmic drug or solution discharging apparatus of claim 1, wherein the opening extends throughout the entire length of the wall.

\* \* \* \* \*